(12) United States Patent
Sangha

(10) Patent No.: US 6,840,911 B2
(45) Date of Patent: Jan. 11, 2005

(54) DNA COLLECTION DEVICE AND STORAGE METHOD

(76) Inventor: Jangbir S. Sangha, 4800 North Hill Dr., Fairfax, VA (US) 22030

(*) Notice: Subject to any disclaimer, the term of this patent is extended or adjusted under 35 U.S.C. 154(b) by 10 days.

(21) Appl. No.: 10/212,447

(22) Filed: Aug. 5, 2002

(65) Prior Publication Data

US 2003/0045814 A1 Mar. 6, 2003

Related U.S. Application Data

(63) Continuation-in-part of application No. 09/865,372, filed on May 25, 2001, now Pat. No. 6,440,087.

(51) Int. Cl.[7] .............................. A61B 5/00; A61B 10/00
(52) U.S. Cl. ...................... 600/582; 600/562; 600/569; 600/573; 604/11; 422/99
(58) Field of Search ................................. 600/562, 570, 600/572, 573, 582, 584, 309, 349, 365, 569; 604/1, 11, 317, 327, 328; 422/56–58, 61, 99, 102; 206/223, 569; 435/6, 287.2

(56) References Cited

U.S. PATENT DOCUMENTS

| | | | | |
|---|---|---|---|---|
| 5,260,031 A | * | 11/1993 | Seymour | .................... 422/101 |
| 5,609,160 A | * | 3/1997 | Bahl et al. | ................... 600/584 |
| 5,714,341 A | * | 2/1998 | Thieme et al. | ................ 435/22 |
| 5,874,045 A | * | 2/1999 | Chisum | ....................... 422/58 |
| 5,900,379 A | * | 5/1999 | Noda et al. | ................. 436/518 |
| 6,150,178 A | * | 11/2000 | Cesarczyk et al. | .......... 436/165 |
| 6,241,689 B1 | * | 6/2001 | Chard et al. | ................ 600/584 |
| 6,248,598 B1 | * | 6/2001 | Bogema | ..................... 436/518 |
| 6,303,081 B1 | * | 10/2001 | Mink et al. | .................... 422/61 |
| 6,365,417 B1 | * | 4/2002 | Fleming et al. | ............. 436/514 |

* cited by examiner

Primary Examiner—Charles Marmor
(74) Attorney, Agent, or Firm—Shughart Thomson & Kilroy P.C.

(57) ABSTRACT

An apparatus and method is provided for collecting a DNA sample from the skin and/or from the oral cavity of a subject, the apparatus comprising a handle mounted absorbent layer supported by a resilient layer and bar codes for association of the sample with identification and evidence documents a storage system is provided to allow sample location using a bar code identifier which avoids removal of the device from storage and avoids disturbing the collected sample.

11 Claims, 6 Drawing Sheets

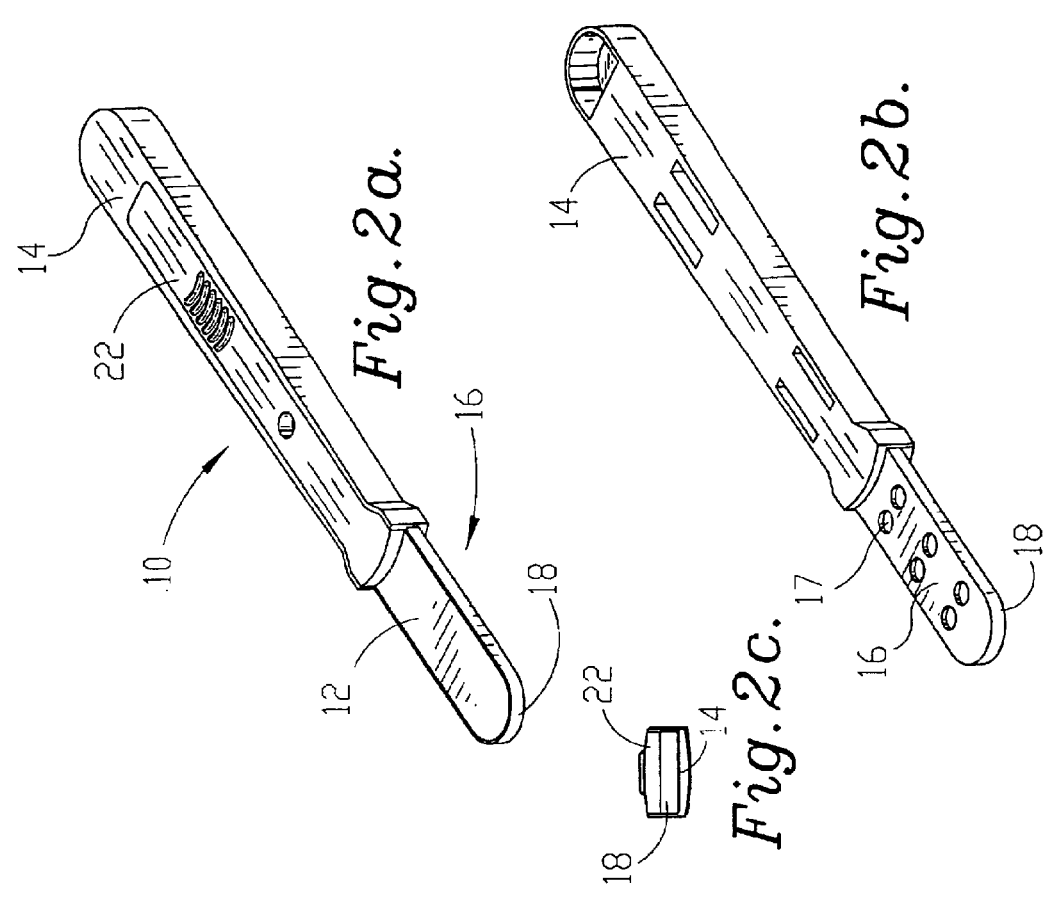
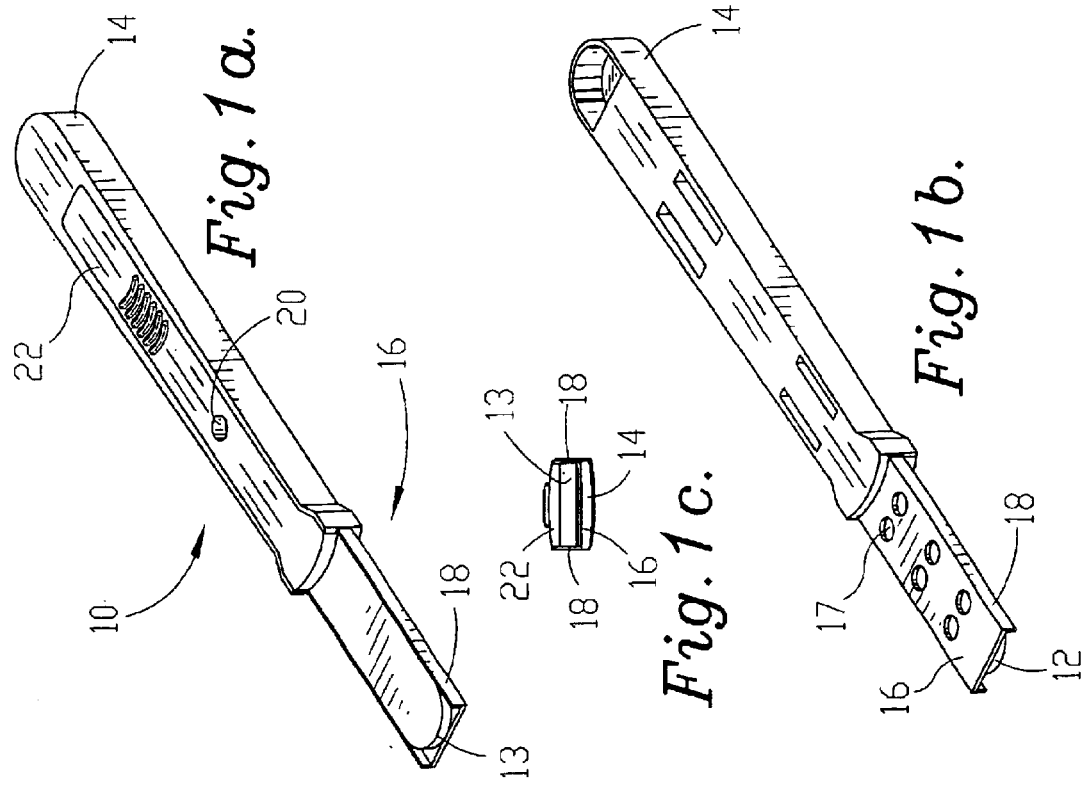

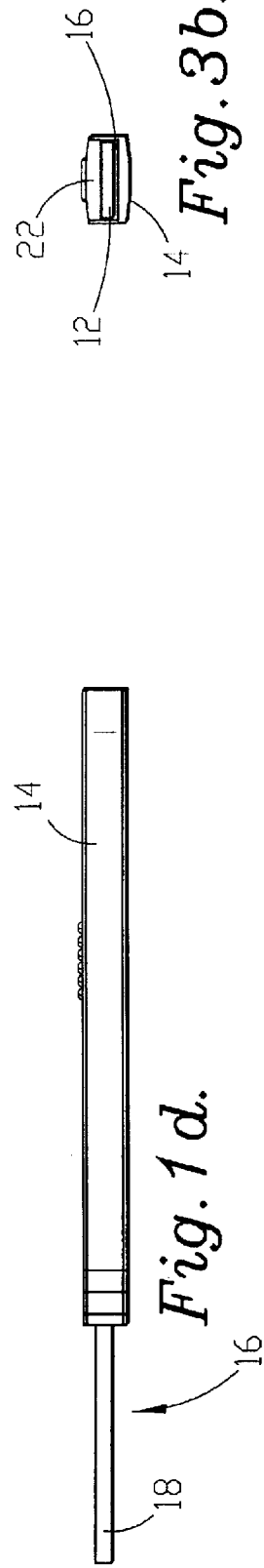
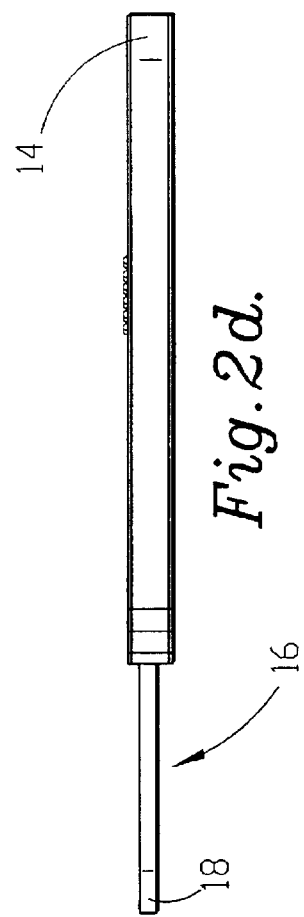
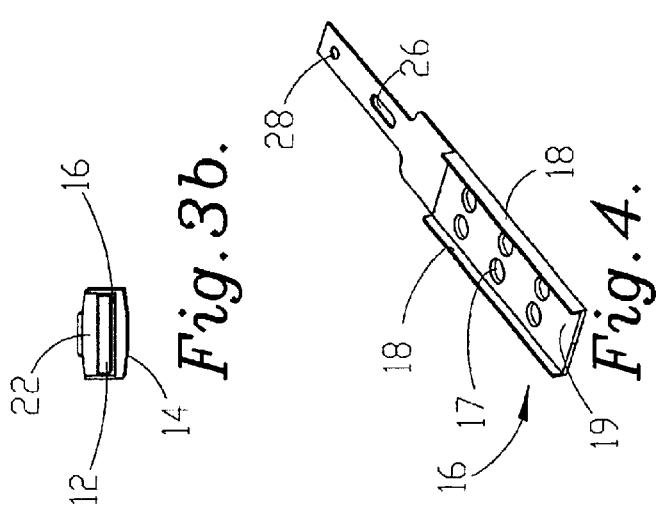
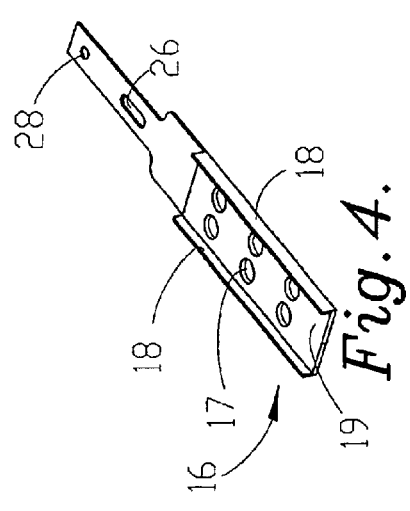
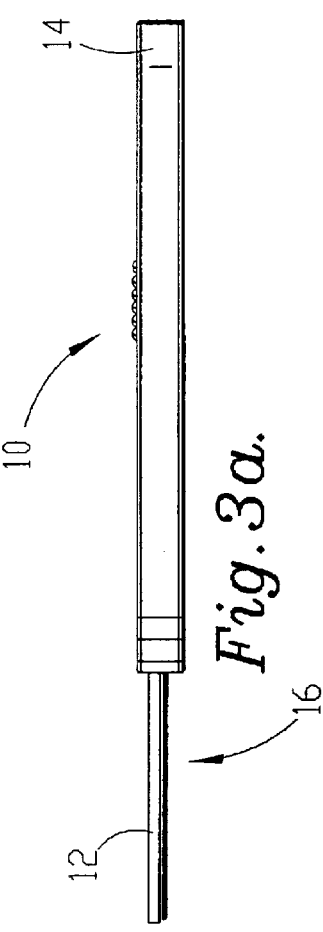
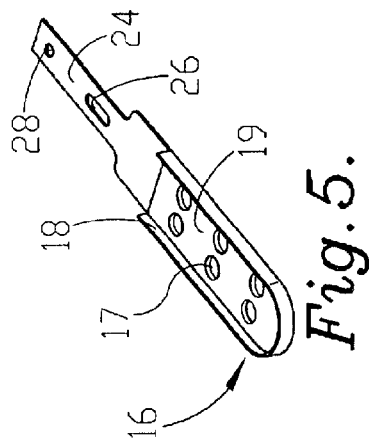

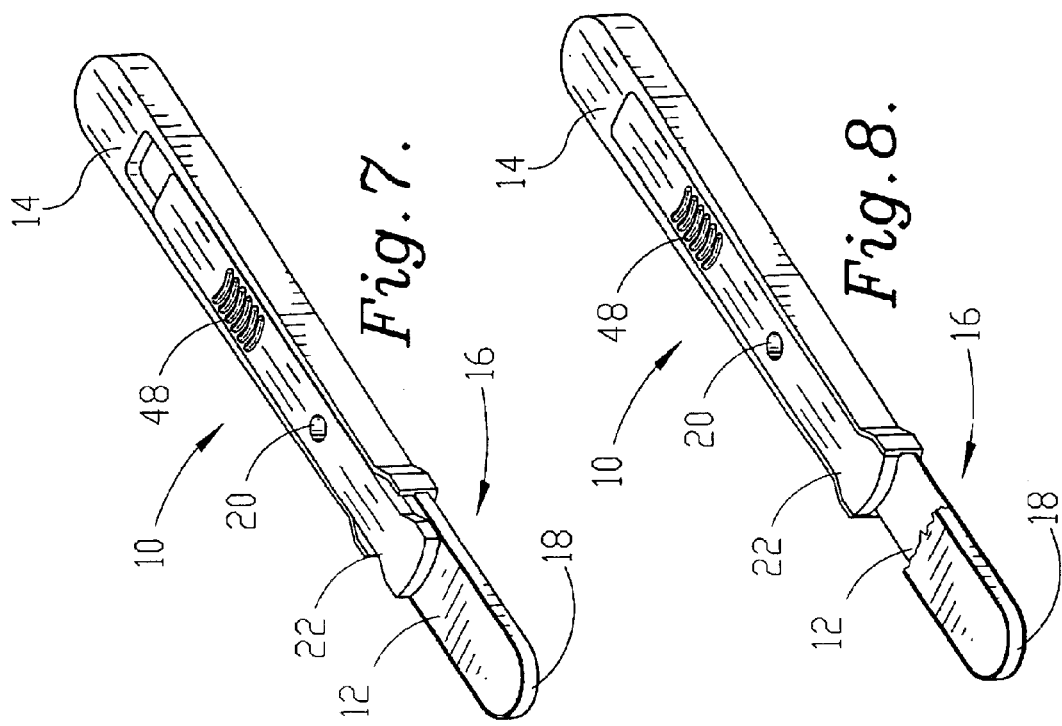
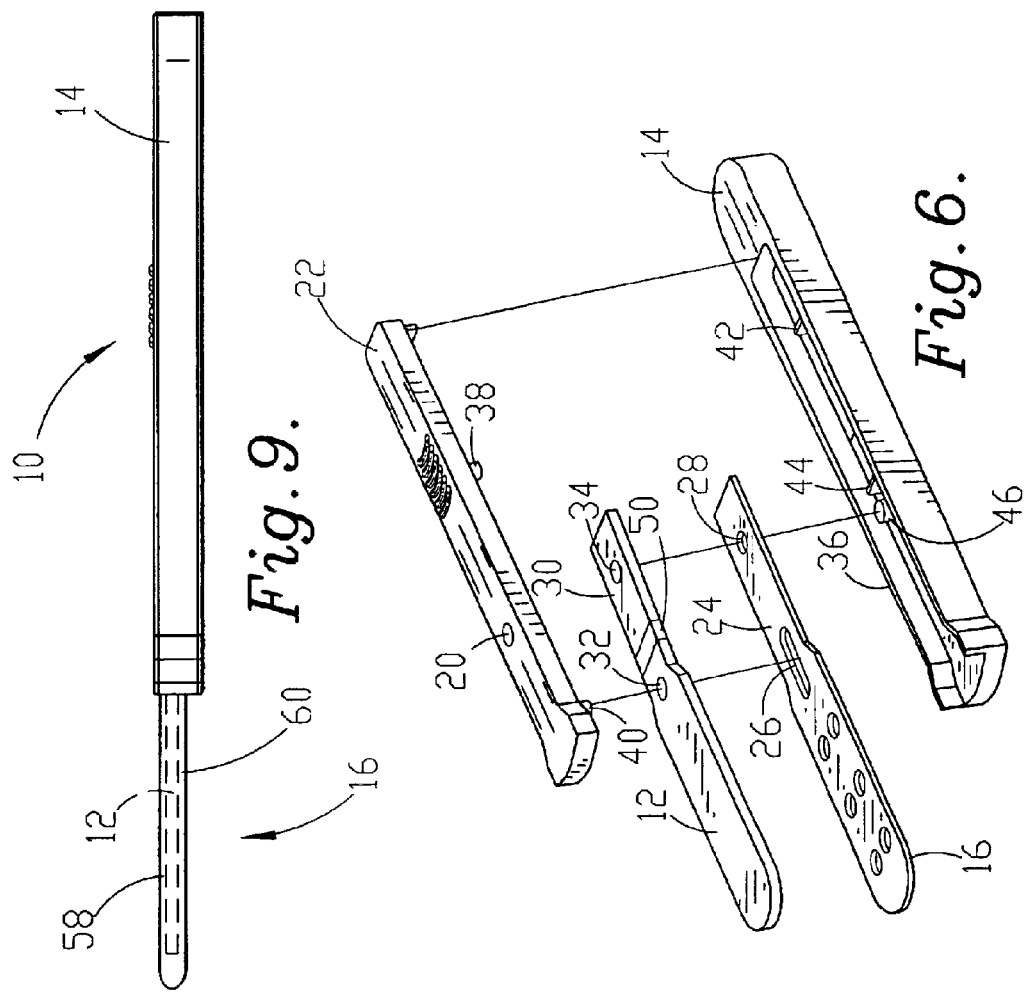

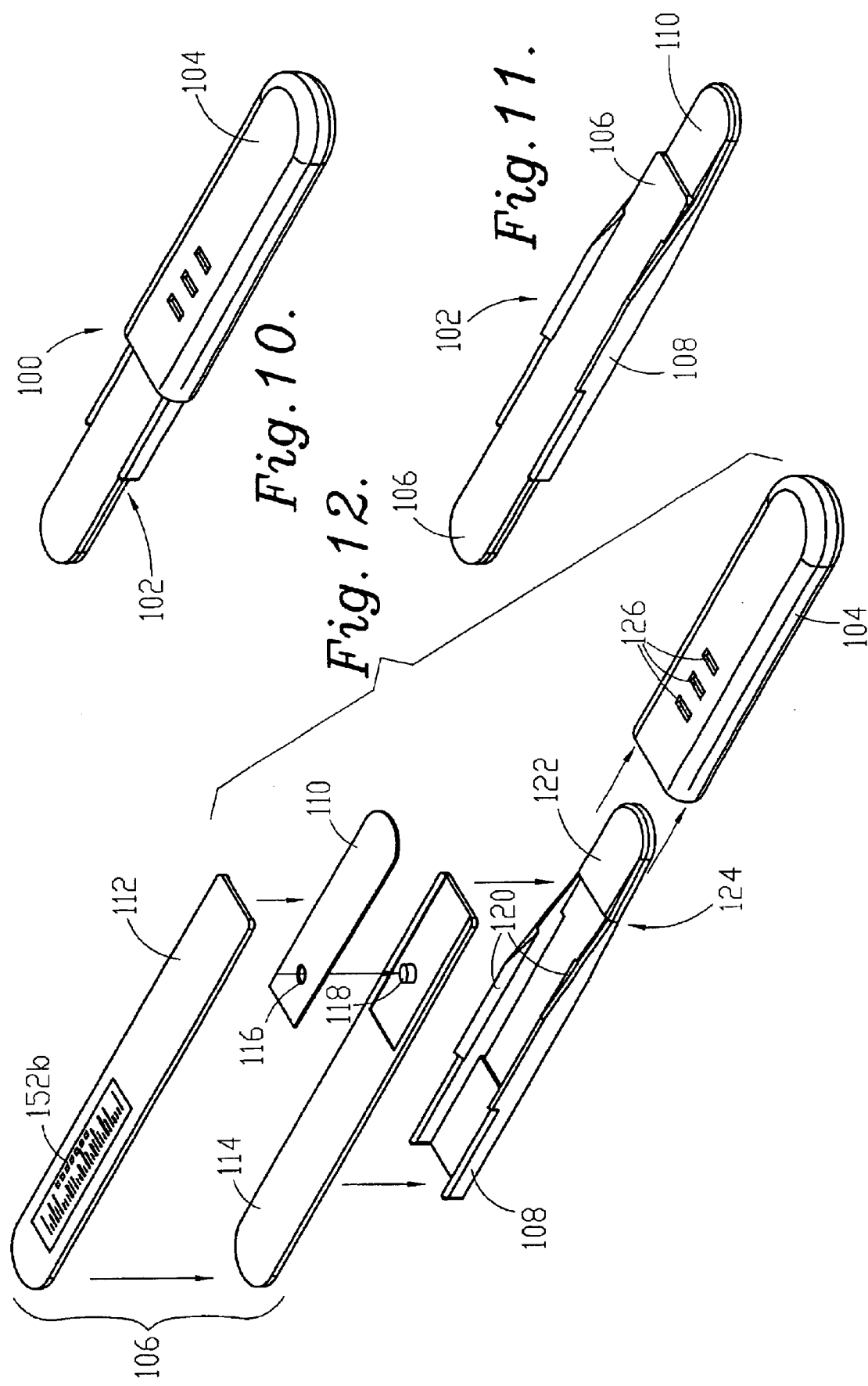

*Fig. 16*

Location: _____
Subject Name: _____ 160
Date Sample Taken: _____

Location Description: _____ 162
_____
_____
_____ 164
_____
_____
_____
_____
_____
_____
                                    166
Sample Appearance at Location:
_____
_____
_____
_____
_____
_____
_____
_____ 168
_____
_____
_____
Date:_____Investigator:_____

Place on DNA Collector
[barcode] D540001

Place on Personal Information Card (White copy)
[barcode] D540001

(Yellow copy)
[barcode] D540001

Place on Specimen Return Envelope
[barcode] D540001

Extra Barcodes
[barcode] D540001
[barcode] D540001
[barcode] D540001
[barcode] D540001

DNA COLLECTION DEVICE AND STORAGE METHOD

This application is a continuation-in-part application of application Ser. No. 09/865,372 filed May 25, 2001, now issued as U.S. Pat. No. 6,440,087 the specification of which is incorporated herein by reference.

FIELD OF THE INVENTION

The field of the present invention is devices for collecting oral fluid samples. In particular, the present invention provides a device having an absorbent for collection of oral fluids thereon and the absorbent having a shield layer positioned adjacent to one side of the absorbent. The shield operates to support the absorbent and to prevent adhesion of the absorbent to the oral tissue or the teeth while the absorbent is within the mouth for collection of an oral fluid sample. In one embodiment of the invention the shield operates to insure that the only oral fluid contacting the absorbent during the collection procedure is saliva. A method of collecting saliva from the buccal cavity is provided which avoids the collection of mucosal transudate. In another embodiment of the invention a device and method of collecting DNA and surface cells that may contain DNA and of storing the DNA samples for later access and use is provided.

BACKGROUND OF THE INVENTION

The buccal cavity of the mouth is that portion of the mouth between the inside of the cheek and the teeth and gums. It has long been recognized that the buccal cavity is a convenient location for the collection of saliva from human beings. One prior example of the use of the buccal cavity as a saliva collection area can be found in Immunoradiometric Assay of Salivary Anti-C3 Antibodies, by Challacombe, Journal of Immunological Methods, (1978), pages 53–59. In the Challacombe article, saliva was collected from neonates by means of a small sterile sponge placed in the mouth between the gum and the cheek. Numerous other methods and devices for collecting saliva have been utilized throughout the years. Typically, these methods for collecting saliva have comprised placement of an absorbent pad or a wad chewable material in the mouth to absorb saliva as the material rested in the mouth or was chewed by the subject.

Recently, investigators have been attracted to methods and devices for collecting oral mucosal transudate (OMT) for the collection and measurement of various analytes which may be present in a subject. Typically the device used for such mucosal transudate collection has consisted of a cotton fiber pad that is placed between the lower gum and cheek and rubbed back and forth along the gum/teeth margin (the gingival interface) followed by analysis of the material absorbed on the cotton wool swab. An example of this type of collection of material on a cotton wool swab from along the gum/teeth margin can be found in diagnosis of Hepatitis A and B by testing saliva, J. V. Parry, et al., Journal of Medical Virology, 28:255–60 (1989).

During the collection of saliva from the mouth, and in particular, the buccal cavity, it is not uncommon for the absorbent to be placed into the buccal cavity or under the tongue and to be allowed to reside there for two or more minutes. During this period of time that saliva is being collected from the mouth, moisture is being removed from the tissue surrounding the absorbent and drawn into the pad. It is not uncommon for this loss of moisture from the tissues adjacent the pad to result in the absorbent pad beginning to adhere or stick to the tissue of the mouth thereby making removal of the absorbent pad difficult or uncomfortable. It is possible for the adhesion of the absorbent pad to the mouth tissue to be sufficiently strong that the attempt to withdraw the absorbent pad from the mouth results in separation of the pad from the handle portion of the apparatus being used to manipulate the absorbent pad. In particular, it is not uncommon that the absorbent pad will be placed in the buccal cavity, and the side of the absorbent pad which is next to the teeth and gums will become stuck to the teeth or the gum tissue. This circumstance is uncomfortable for the patient and can result in separation of the absorbent pad from the handle when removal of the saliva saturated absorbent pad from the mouth is attempted.

The present invention solves the problem of adhesion of the absorbent pad to oral tissue and at the same time provides a support structure to prevent un-wanted tearing of the absorbent away from the device handle. Further, the present invention provides investigators with a means of isolating fluid absorption from areas of the mouth from which collection is not desired. In particular, one embodiment of the present invention prevents the absorbent from contacting the gingival interface at the junction of the teeth and gums and thereby prevents collection of OMT or oral mucosal transudate.

SUMMARY OF THE INVENTION

The present invention eliminates or greatly reduces the instances of adhesion of an absorbent pad to tissues that are adjacent to one side of the pad. Also, the present invention provides additional structural support for an absorbent pad once it has become saturated with an oral fluid such as saliva. A further advantage of the present invention is that one side of the absorbent pad can be shielded from contact with adjacent oral tissues thereby preventing absorption of an oral fluid onto the shielded side of the absorbent pad as a result of direct contact by the pad with the adjacent oral tissue.

The above benefits and objectives are accomplished in the present invention by an oral fluid collection device which provides, in one embodiment, a non-absorbent layer or shield which is applied to, or is adjacent to, one side of an absorbent pad. In another embodiment, a different combination of the benefits of the present invention are accomplished by use of a fluid shield or fluid-impervious layer which is provided with voids in the shield layer. The voids allow analytes that are dissolved in saliva to pass through the shield layer and to be absorbed by the pad while the shield prevents adhesion of the absorbent to the adjacent oral tissue. In addition, mouth fluids which must be rubbed off of tissues (e.g., OMT) are not collected by the pad.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

DESCRIPTION OF THE DRAWINGS

Preferred embodiments of the invention, illustrative of the best modes in which the applicant has contemplated applying the principles, are set forth in the following description and are shown in the drawings and are particularly and distinctly pointed out and set forth in the appended claims.

FIG. 1a is a top and side perspective view of a first embodiment of the invention and having a shield having side walls and an open front;

FIG. 2a is a top and side perspective view of a second embodiment of the invention having a shield with a continuous side wall covering the sides and front of the absorbent;

FIG. 1b is a bottom and side perspective view of the embodiment of FIG. 1a and showing a series of voids in the shield to allow passage of liquids to the absorbent;

FIG. 2b is a bottom and side perspective view of the embodiment of FIG. 2a also showing the inclusion of voids in the shield to allow passage of fluids to the absorbent layer;

FIG. 1c is a front an elevational view of the embodiment of FIG. 1a;

FIG. 2c is a front and elevational view of the embodiment of FIG. 2a;

FIG. 1d is a side elevational view of the embodiment of FIG. 1a;

FIG. 2d is a side elevational view of the embodiment of FIG. 2a;

FIG. 3a is an alternative embodiment of the present invention having a shield without side walls;

FIG. 3b is a front and elevational view of the embodiment of FIG. 3a;

FIG. 4 is a top and side perspective view of the shield portion of the embodiment of FIG. 1a;

FIG. 5 is a top and side perspective view of the shield portion of the embodiment of FIG. 2a;

FIG. 6 is an exploded view of the embodiment of FIG. 3a;

FIG. 7 is a top and side perspective view of the embodiment of FIG. 3a showing the separator shaft of the handle extended to break the absorbent away from the handle;

FIG. 8 is a top and side elevational view of the embodiment of FIG. 3a after the extension of the separator shaft shown in FIG. 7 and the subsequent retraction of the separator shaft and showing the separation of the absorbent from capture within the handle to allow removal of the absorbent;

FIG. 9 is a side elevational view of another embodiment of the invention in which the absorbent has a separation line to permit manual breaking-away of a portion of the absorbent, the embodiment of FIG. 9 can comprise a shield that is impervious to fluids on one side with no shield on the other side or it can comprise a shield that is impervious to fluids on one side while having a covering with micro pores on the other side or it can comprise a shield made of a substance having micro pores that completely covers the absorbent.;

FIG. 10 is a top and side perspective view of an embodiment of a DNA collection device with the cover in place over the end of the device;

FIG. 11 is a top and side perspective view of the DNA collection device of FIG. 10 with the cover removed;

FIG. 12 is an exploded view of the DNA collection device of FIG. 10;

FIG. 16 shows a specimen collection information form which may be used by a technician or a DNA collector with the device of the present invention, the form having multiple bar code identifier labels thereon for attachment to the various collection devices used in collecting samples and for attachment to other forms and materials related to evidence collection to allow association between all collection devices and investigator reports and photographs and reports.

DESCRIPTION OF THE PREFERRED EMBODIMENT

Figure 15:
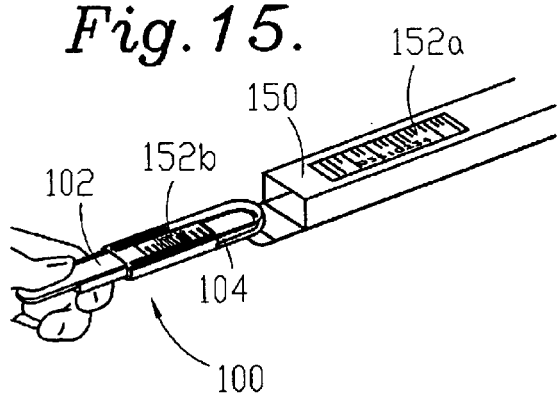
FIG. 15 is a perspective view of a DNA collection device having a bar code identifier available for scanning.

Referring now to FIG. 1a, oral sample collection device 10 of the present invention is comprised of absorbent layer 12 which is attached to handle 14 by capture of a tail piece or absorbent tongue portion 30 (FIG. 6) between handle 14 and separator shaft 22 which is slidably captured within handle 14. Absorbent 12 is comprised of any material which is suitable for collection of saliva. Examples of acceptable absorbent materials are cellulose fiber such as paper or cotton or nylon or polyester absorbent pads. Examples of absorbent papers which are appropriate for the present invention include those manufactured by S & S® 903™ manufactured by Schleicher & Schuell, Inc. or equivalent papers from other vendors such as Whatman, Inc. of Clifton, N.J. Still referring to FIG. 1a, absorbent 12 is generally formed of a sheet of absorbent paper approximately ½ inch wide and 2½ inches long and 1/16 inch in thickness. Absorbent 12 is generally comprised of a first or top surface and a second or bottom surface which are joined by absorbent connecting edge 13. Adjacent the bottom or lower surface of absorbent 12 is plastic guard or shield 16. In the embodiment of FIG. 1a, shield 16 is provided with upturned side walls 18 which extend upwardly along edge 13 of absorbent 12. Shield 16 protects one surface of absorbent 12, in this case, the lower surface and a portion of absorbent edge 13 from contact with adjacent oral tissues.

It is desirable, but not necessary, that shield 16 be comprised of a thin, sheet plastic material which is slightly soft and flexible and safe that damage to oral tissues is avoided. Generally, any fluid impervious material would be satisfactory for use in forming shield 16 as long it is safe to be used in the mouth. It is also contemplated that shield 16 could be formed as part of absorbent 12 by using a plastic coating directly on absorbent 12. In an alternative embodiment, in which shield 16 encloses absorbent 12 by covering the top and the bottom surfaces and edge 13 of absorbent 12, shield 16 can be formed from a material that acts as a molecular sieve to differentially permit molecules to pass through shield 16 to absorb on absorbent 12 depending upon the molecule size. A useful material for this embodiment is cellulose acetate. Cellulose acetate is manufactured in several forms by several different manufacturers. The different forms allow passage through the cellulose acetate of molecules of a particular size range while excluding molecules of other sizes. An example of a suitable cellulose acetate material is a molecular porous membrane product called Spectra/Por manufactured by The Spectrum Companies of Gardena, Calif. An alternative molecular porous membrane material is polyvinylideneflouride (PVDF).

Therefore, a form of cellulose acetate can be selected to form shield 16 which allows passage through the cellulose acetate shield 16 of a molecule of interest while excluding other molecules from reaching absorbent 12. In one particular application, the molecular porous membrane product could be selected to insure the exclusion of selected sizes of proteins from surrounding oral fluid while allowing passage other analytes of interest through the shield 16 for absorption on absorbent 12. The function of shield 16 will be discussed in further detail hereinafter.

Still referring to FIG. 1a, device 10 can be provided with a means for determining when a sufficient amount of sample has been collected and for determining whether or not the sample collected is, in fact, saliva. The method of determining that the specimen collected is, in fact, saliva and that a sufficient amount of saliva has been collected is the subject of U.S. Patent No. 5,334,502 and is incorporated herein by reference. In summary, the method of determining that a sufficient quantity of saliva has been collected can be as simple as utilizing a colored vegetable dye which will migrate along the absorbent paper as the saliva is absorbed onto absorbent 12 and the saliva migrates toward handle 14. In such a case, absorbent 12 will extend up into handle 14 past observation window or void 20 which is placed in handle 14. As the saliva front moves along absorbent 12 and into handle 14 where the tail portion of the absorbent is captured by handle 14, the colored vegetable dye or other suitable indicator will dissolve in the saliva and be pushed deeper into the interior of handle 14 until it is visible within void or window 20 of handle 14. When the dye is visible in window 20, the user of collection device 10 is assured that sufficient saliva has been applied to absorbent paper 12 to wet the absorbent 12 as far as window 20. If the absorbent has been properly sized, sufficient sample will have been collected to perform the desired subsequent analysis on the saliva.

Alternatively, and as explained in U.S. Pat. No. 5,334,502, the simple vegetable dye can be replaced with a chemical compound which is reactive with the component of saliva. Typically, upon contacting the saliva, the chemical component will undergo a change of color in response to a chemical reaction with a component of saliva. In this manner, the observation of the color change in the indicator demonstrates to the operator of collection device 10 that it is, in fact, saliva on the absorbent paper and not a substitute liquid such as water.

Referring now to FIG. 1b, the bottom side of device 10 of FIG. 1a is shown. In FIG. 1b, shield 16 is shown extending from handle 14. Shield 16 covers the bottom surface of absorbent 12 and sidewalls 18 of shield 16 is shown extending to cover edge 13 of absorbent 12. In FIG. 1b, shield 16 of the embodiment shown is further comprised of shield voids 17. Shield voids 17 are openings within shield 16 which allow fluids, such as saliva, to pass through shield 16 and be absorbed on absorbent 12. In this manner, shield 16 serves its general purpose of maintaining separation of absorbent 12 from adjacent mouth tissues while allowing saliva to pass through shield 16 to expedite the saturation of absorbent 12 with oral fluids such as saliva.

As previously described, the ability of the present invention to maintain separation between oral tissues and absorbent 12 is important for several reasons. As has been described in the background of the invention, it is often the case that during the time an oral fluid collection device is held in the mouth, the absorbent will adhere to oral tissues which are in contact with absorbent 12. When the collection period is at an end, and the user attempts to withdraw the oral collection device from the mouth the absorbent may continue to adhere to the oral tissues. As the absorbent now has become wetted with saliva and is less resilient, the absorbent will tend to tear off the handle to which it is attached and remain in the mouth due to the adhesion between the absorbent and the oral tissues.

Another purpose of shield 16 is to provide additional physical support to absorbent 12 while it is within the mouth and after it has absorbed saliva. When absorbent 12 is in the mouth, it absorbs saliva and becomes heavy and limp. In this state, the absorbent can easily be torn by pressure applied to it. The presence of shield 16 reinforces pad 12 and adds support to the saturated absorbent and assists in preventing undesired tearing of absorbent 12 from handle of oral fluid collection device 10. Another useful aspect of shield 16 is the separation shield 16 maintains between absorbent 12 and any surface upon which device 10 is placed. While device 10 should not be placed onto a surface prior to being used, it may be necessary, once the device has absorbed saliva and is withdrawn from the mouth to momentarily set device 10 down on a table surface or the like. In the absence of shield 16, the wetted and flexible absorbent would droop down and contact whatever surface device 10 was set upon. This contact with the surface upon which device 10 was placed would undesirably contaminate absorbent 12. In this situation, shield 16 acts as a supporting shelf which holds wetted absorbent 12 away from any adjacent surface upon which oral collection device 10 might be placed. Another important feature of shield 16 is the ability of shield 16 to prevent contact between absorbent 12 and particular mouth tissues. In recent years, some investigators have found it useful to rub absorbents against the gum tissues, specifically at the gingival interface, to collect oral muscosal transudate. It is believed that oral muscosal transudate or OMT presents higher concentrations of various analytes of interest than does saliva. However, saliva has been collected for many years from the buccal cavity of the mouth, and a substantial body of evidence and data has been developed over the years which relate to the concentration of various analytes contained in saliva from the buccal cavity.

Therefore, it is useful for investigators to be able to conclusively distinguish the collection of saliva from the buccal cavity and to rule out any collection of OMT while collecting at that location within the mouth. This is accomplished with the present invention by use of shield 16 which, in one of its various embodiments, can allow the passage of saliva only to the absorbent such as the embodiment in which void 17 (FIG. 1b) are included in shield 16. Alternatively, any collection of OMT can be eliminated by the use of an embodiment of shield 16 which has no voids 17 within the shield. In this manner, absorbent 12 is completely shielded from any contact with the gum tissue when the device is properly oriented within the mouth so as to place the shield against the gums. In this orientation collection of OMT is absolutely eliminated and only saliva is collected from the non-shielded surface which is adjacent the inside of the subject's cheek.

Referring now to FIG. 1c, a front end elevational view of the embodiment of FIGS. 1a and 1b is shown. In FIG. 1c, it is shown that shield 16 of the embodiment of FIG. 1a and 1b fully protects the bottom of absorbent 12 and that shield sidewalls 18 extend upwardly to protect the side portions of absorbent edge 13 while leaving the front of absorbent edge exposed. Examination of FIG. 1d shows the complete coverage of absorbent edge 13 by shield sidewall 18. It will be appreciated that the embodiment of the present invention shown in FIG. 1a and 1b and the shield 16 shown therein can be provided with shield voids 17 as shown in FIG. 1b or shield 16 can exclude the use of shield voids 17 and present a solid and impenetrable surface. This is dependent upon the particular investigator's wishes and whether the investigator desires to slightly more rapidly collect saliva and saturate absorbent 12 when shield voids 17 are included in shield 16. In either embodiment, that is, embodiments of shield 16 including shield voids 17 or embodiments of shield 16 which present a solid surface, the collection of OMT is avoided as in both embodiments of shield 16, prevent contact between absorbent 12 and the interface between the teeth and gums is avoided.

Referring now to FIG. 2a and 2b, an alternative embodiment of oral fluid collection device 10 is shown. In the embodiment of FIG. 2a and 2b and 2c, shield 16 has a flat protective bottom surface shown in FIG. 2b and has a continuous shield sidewall 18 which protects the entirety of absorbent edge 13 of absorbent layer 12. In the embodiment of FIGS. 2a, 2b and 2c, shield sidewall 18 wraps completely around absorbent edge 13 to prevent any contact between the bottom surface of absorbent 12 and absorbent edge 13. In this manner, the only portion of absorbent 12 which can contact oral tissue is the top surface as shown in FIG. 2a. In FIG. 2b, it can be seen that shield 16 is provided with voids 17 to allow absorption of oral fluids such as saliva at the bottom surface of absorbent 12. It will be appreciated from the previous discussion that shield 16 in the embodiment of FIGS. 2a and 2b can be provided with either void 17 or shield 16 can be a solid surface which excludes passage of saliva through shield 16 to contact absorbent 12. FIG. 2c shows a front end elevational view of the embodiment of FIGS. 2a and 2b and shows the shield sidewall 18 covering the front portion of absorbent edge 13 of absorbent 12. In FIG. 2d, it can be seen that shield sidewall 18 protects the entire length of absorbent edge 13 of absorbent 12.

Referring now to FIG. 3a, an alternative embodiment of the present invention is shown wherein a flat, plastic guard or shield 16 is used to protect the lower side of absorbent 12 from contact with adjacent tissue. In the embodiment of FIG. 3a, shield 16 is comprised of the same materials as is shield 16 of the embodiments shown in FIG. 1a and 2a. However, shield 16 of the embodiment of FIG. 3a is a flat sheet and does not have shield sidewalls 18 to protect edge 13 of absorbent 12 from contact with oral tissue. In practice, the embodiment of FIG. 3a may be used when there is less concern over the need to exclude the collection of other oral fluids, for example, when the oral fluid sampling is to be conducted under the tongue. When collecting oral fluid from under the tongue, device 10 is placed such that one surface of absorbent 12 is oriented towards the tongue and the other surface of absorbent 12 is placed against the floor of the mouth. In this collection method, edges 13 of absorbent 12 will not contact oral tissue sufficiently to adhere thereto. In this collection method, flat, plastic guard 16 of embodiment FIG. 3a is sufficient to protect one of the large surfaces of absorbent 12 from contact with the adjacent oral tissue and adhesion to the tissue is prevented. Upon the absorbent being saturated with saliva, device 10 of FIG. 3a can be easily withdrawn from the mouth without damage to absorbent 12.

Referring now to FIGS. 4 and 5, the construction of shield 16 is shown. In FIG. 4, the shield utilized in the embodiment of FIGS. 1a and 1b is shown, and in FIG. 5, the shield utilized in the embodiment of FIGS. 2a and 2b is shown. Shield 16 shown in FIGS. 4 and 5 is comprised of shield floor 19 to which shield tongue 24 extends rearwardly. In the embodiment of FIG. 3a, shield 16 is comprised of these two principal elements and does not have the shield sidewall 18 element. As previously discussed, attached to shield floor 19 is shield sidewall 18 which can be embodied as two straight sidewalls 18 as shown in FIG. 4, or can be embodied as a continuous sidewall 18 as shown in FIG. 5 and which protects both sides and the front of absorbent edge 13 of absorbent layer 12 when the absorbent layer is placed within shield 16 of FIG. 5. Each embodiment of shield 16 is equipped with shield tongue 24 which extends rearwardly from shield floor 19 and is captured within the structures provided in handle 14 and separator shaft 22. The utility and purpose of this capturing tongue 24 within handle 14 will be thoroughly described hereinafter. Shield tongue 24 is provided with two voids. A first void is shield tongue securing void 28 which is at the rear of shield tongue 24. A second void is shield tongue oval or elongate void 26 which is in a forward position on shield tongue 24.

Referring now to FIG. 6, the construction and utility of the various components comprising shield 16 and absorbent 12 will be discussed. FIG. 6 is an exploded view of the present invention and is essentially the same for all embodiments of the invention discussed herein. The exploded view generally shows handle 14, shield 16 which is fitted within handle 14, absorbent 12 which is fitted within handle 14 on top of shield 16, and separator shaft 22 which is press fitted into separator track 36 of handle 14 where it is slidably held in place by compression fit.

The assembly and operation of device 10 will now be described. Shield 16 is placed within handle 14 such that securing post 46 of handle 14 projects through shield tongue securing void 28 at the rear of shield tongue 24 of shield 16. The engagement between securing post 46 and shield tongue securing void 28 ensures that shield 16 cannot be inadvertently pulled away from handle 14. Once shield 16 is placed within handle 14, absorbent layer 12 is then placed on top of shield 16 and positioned such that securing post 46 of handle 14 which is projecting through shield tongue securing void 28 of shield 16 captures absorbent tongue securing void 34. Absorbent securing void 34 serves to hold absorbent 12 in place within handle 14 and avoids absorbent 12 from being inadvertently pulled away from handle 14. It will be appreciated that absorbent 12 is positioned within handle 14 to affect registration or alignment between absorbent tongue front void 32 and shield tongue oval or elongate void 26. The desired alignment is that absorbent front void 32 be directly above the rear of shield tongue oval void 26. The purpose of this alignment will be described hereinafter.

After shield 16 and absorbent 12 have been placed in registration and in handle 14 and secured upon securing post 46, separator shaft 22 can then be press fitted into handle 14. As separator shaft 22 is fitted into handle 14, separator shaft rear post is positioned in handle 14 between handle rear stop 42 and handle forward stop 44. Separator shaft front post 40 extends through absorbent tongue front void 32 and into shield tongue oval void 26. Once the alignment of separator shaft 22, which has just been described, is achieved, separator shaft 22 is compressively fitted into handle 14 where it is held in place by separator track edges 36 which are the edges of a void within handle 14 that is designed to receive separator shaft 22 therein. Once separator shaft 22 is fitted within handle 14, it is to be understood that separator shaft 22 is slidably mounted within handle 14 and can be pushed in a forward direction whereupon forward movement is terminated by separator shaft rear post 38 contacting handle forward stop 44. In the reverse movement, the sidling of separator shaft 22 within handle 14 is stopped by separator shaft rear post 38 contacting handle rear stop 42.

Referring now to FIGS. 7 and 8, the function and purpose of the slidable mounting of separator shaft 22 within handle 14 will be described. In general, the purpose of the slidable mounting of separator shaft 22 within handle 14 is to accomplish the separation of absorbent 12 from its attachment within handle 14. The detachment of absorbent 12 from handle 14 is desired once absorbent 12 has become saturated with saliva and it is desired to detach saturated absorbent 12 from handle 14 so that the saliva saturated absorbent may be placed in a preservative solution or utilized in whatever manner to test for analytes in the saliva. To detach absorbent 12 from handle 14, the operator grasps handle 14 and, using thumb pressure on ridges 48 of separator shaft 22, slides separator shaft 22 toward absorbent 12. The forward movement of separator shaft 22 within handle 14 causes separator shaft front post 40, which is engaged within absorbent tongue front void 32, to create a forward pressure on the portion of absorbent 12 which is in front of absorbent front tongue void 32. By contrast, the portion of absorbent tongue 30 which is to the rear of absorbent front tongue 32 is held in place by capture of absorbent tongue securing void 34 by handle securing post 46. The pressure that is created by the forward movement of separator shaft front post 40 against absorbent tongue front void 32 causes the portion of absorbent 12 which is in front of separator shaft front post 40 to tear away from the portion of absorbent tongue 30 which is to the rear of absorbent tongue front void 32. The portion of absorbent 12 which has been separated is pushed forward by the movement of separator shaft 22 within separator shaft track 36. Once the forward movement of separator shaft 22 has been terminated by separator rear post 38 contacting handle forward stop 44 (FIG. 7), separator shaft 22 can be pulled rearwardly by thumb pressure on ridges 48 to reposition separator shaft 22 within handle 14. Repositioning separator shaft 22 within handle 14 is terminated by separator shaft rear post 38 contacting handle rear stop 42. (FIG. 8.) At the conclusion of the above procedure, the saturated absorbent 12 is separated from absorbent tongue 30 which is contained within handle 14 and the separated portion of absorbent layer 12 is left residing on shield 16 as shown in FIG. 8. Now that the user has separated absorbent layer 12 from handle 14, the separated portion of absorbent 12 may be shaken off of shield 16 and into a preservative solution.

The method of operation of the present invention is as follows, sample collection device 10 which can contain any of the shield embodiments described herein is removed from a protective packaging and absorbent layer 12 is inserted into the mouth. Absorbent layer 12 can be placed in several different locations within the mouth such as underneath the tongue or in the buccal cavity, or if desired, absorbent 12 can be placed on top of the tongue. Sample collection device 10 is allowed to remain in the selected location of the mouth for sufficient time to permit absorption of saliva. Should an embodiment of sample collection device 10 be used which includes the indicator which has been previously described in U.S. Pat. No. 5,334,502 and which is incorporated here by reference, the operator can simply rely on viewing the appearance of the indicator within window 20 of device 10. The operation of the indicator is such that as saliva is absorbed onto absorbent 12, it migrates toward absorbent tongue 30 (FIG. 6). Along the length of absorbent tongue 30 and before the portion of absorbent tongue 30 which is viewable through window 20, an indicator 50 is placed on absorbent tongue 30. The migration of the saliva along absorbent tongue 30 moves indicator 50 into position to be observed through window 20 when sufficient saliva has been absorbed onto absorbent 12 to achieve migration of indicator 50 along absorbent tongue 30 to reposition indicator 50 within window 20. Thus, either using the indicator method or by simply timing the length of time the absorbent is in contact within the mouth, the operator determines that sufficient saliva has been collected on absorbent 12 and device 10 is removed from the mouth. The operator then effects separation of the front portion of absorbent 12 from the tongue portion 30 of absorbent 12 by pushing forward on separator shaft 22 to cause separation between the front and rear areas of absorbent 12 at the location of absorbent tongue front void 32 and the portion of absorbent 12 in front of absorbent front void 32 is pushed in a forward direction by separator shaft 22 and is detached from absorbent tongue 30. The operator may then remove the separated portion of absorbent 12 from collection device 10 and place the detached absorbent into a preservative solution or into such other container as is desired.

Referring now to FIG. 9 an alternative embodiment of the present invention is provided which does not rely upon the use of the separator shaft 22 to release the absorbent from capture in handle 14. In the FIG. 9 embodiment of the invention the absorbent is provided with a separation line 60 which permits manual breaking-away of a portion 58 of absorbent 12 from handle 14 of device 10. After portion 58 is removed from absorbent 12 by the user applying tearing or shearing force to handle 14 and portion 58 to cause separation of portion 58 at separation line 60, the user can then insert portion 58 into a preservative solution or use portion 58 separately from handle 14. It will also be appreciated that is separation line 60 is placed in the middle of absorbent 12, either parallel to the longitudinal axis of the absorbent or orthogonally to the longitudinal axis, that absorbent 12 can then provide two useful portions for user testing or storage.

It should be appreciated that the embodiment of FIG. 9 can further comprise a shield that is of any of the types previously described. For example, the shield can be impervious to fluids on one side with no shield on the other side or it can comprise a shield that is impervious to fluids on one side while having a covering that contains micro pores on the other side or it can comprise a shield made of a substance having micro pores that completely covers the absorbent. FIG. 9 particularly, shows an embodiment having a shield of a substance with micro pores that completely covers the absorbent while the absorbent is provided with separation line 60.

Referring now to FIG. 10, an alternative embodiment 100 is shown which is adapted for the collection of DNA or skin cells or epithelial cells which may contain DNA from a subject. Such cells are useful in performing DNA analyses, and it is often desired to make such cell or tissue collections when police officers are engaged in collecting evidence from an investigation or from arrested individuals. Still referring to FIG. 10, DNA collection device 100 is comprised of a collector portion 102 and a cover portion 104. Cover portion 104, as shown in FIG. 12, is adapted to be placed over collector portion 102 to protect the sample collected thereon.

Referring now to FIG. 11, collector portion 102 will be described in greater detail. Collection portion 102 is comprised of a handle portion 106 which is captured within carrier 108. Extending from handle 106 and in contact with carrier 108 is absorbent 110. Absorbent 110 is disposed within DNA collection device 100 for receiving skin cells or epithelial cells thereon during the process of DNA collection.

Referring now to FIG. 12, the construction and assembly of DNA collection device 100 will be described. Handle 106 of DNA collection device 100 is comprised of top handle portion 112 which connects to bottom handle portion 114. Absorbent 110 is held between top handle portion 112 and bottom handle portion 114. In the present embodiment, absorbent 110 is provided with void 116 which fits over securing peg 118 on bottom handle portion 114. Securing peg 118 serves to securely retain absorbent 110 between handle top portion 112 and handle bottom portion 114. However, those skilled in the art will appreciate that many ways of mounting or retaining absorbent 110 in handle 106 are well known within the art and can be easily substituted for the structure of the present embodiment. Once handle top portion 112 is connected with handle bottom portion 114 to secure absorbent 110 therebetween, handle 106 containing absorbent 110 is inserted into carrier 108 for use in collecting a DNA sample. As will be appreciated by examining FIG. 12, handle 106 is press fitted into carrier 108 and retained in carrier 108 by securing members 120 on either side of carrier 108. The proper assembly of handle 106 within carrier 108 places the exposed portion of absorbent 110 in contact with support 122 of carrier 108. Support 122 of handle 108 provides a resilient structure for absorbent 110 to rest against to thereby support absorbent 110 when absorbent 110 is being rubbed against the skin of the subject or the cheek of the subject during collection of a DNA sample from a subject. It will also be appreciated that when a DNA sample is being collected on absorbent 110 by rubbing absorbent 110 against the skin of a subject, the individual using DNA collection device 100 can place a finger against the backside 124 of support 122 to allow a slight pressure to be provided to assist in the dislodging of skin cells from the subject and onto absorbent 110. Both before and after collecting a DNA sample with DNA collector 100, cover 104 is placed onto collector 102 to protect absorbent 110 from contamination and from damage or from cross contamination after a DNA sample has been collected on absorbent 110. On the occasions when the DNA sample is collected onto absorbent 110 by rubbing absorbent 110 against the inside of the cheek of the subject, cover vents 126 are provided in cover 104 to allow air circulation proximate to absorbent 110 to assist in drawing absorbent 110 when it has become moist from the collection of a DNA sample from the inside of a subject's cheek. After the DNA sample or sample of cells which may contain DNA has been collected on absorbent 110 and the device sent to laboratory for testing, handle 106 may be removed from carrier 108 to permit portions of absorbent 110 to be removed—such as with a hole punch—to facilitate testing of the specimen collected on absorbent 100.

Figure 13:
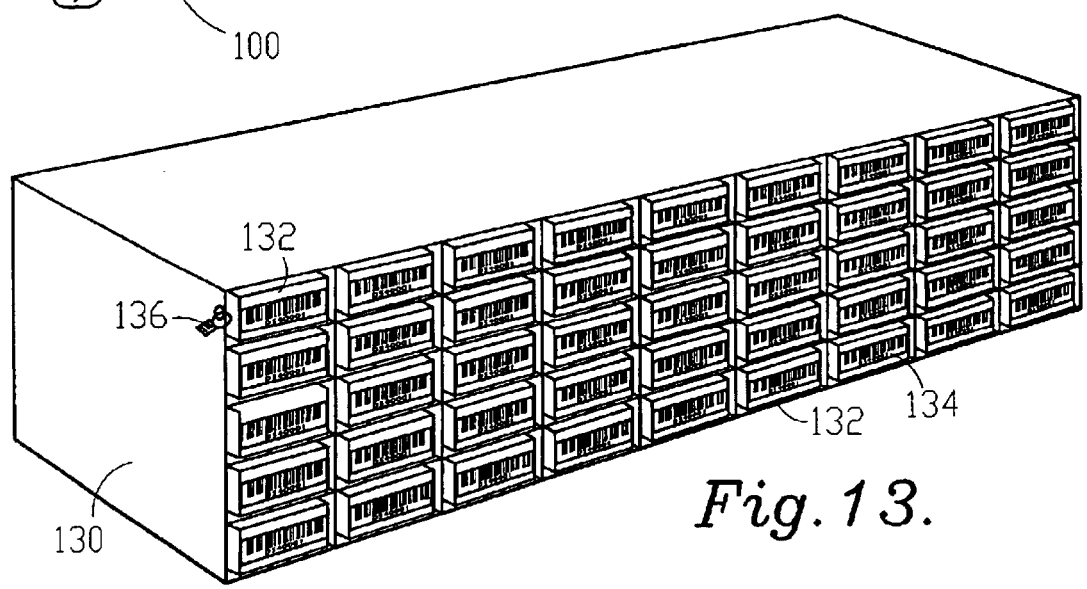
FIG. 13 is a top, left side and front perspective view of an embodiment of a storage system for a plurality of DNA collection devices having a bar code identifier available for scanning.
Figure 14:
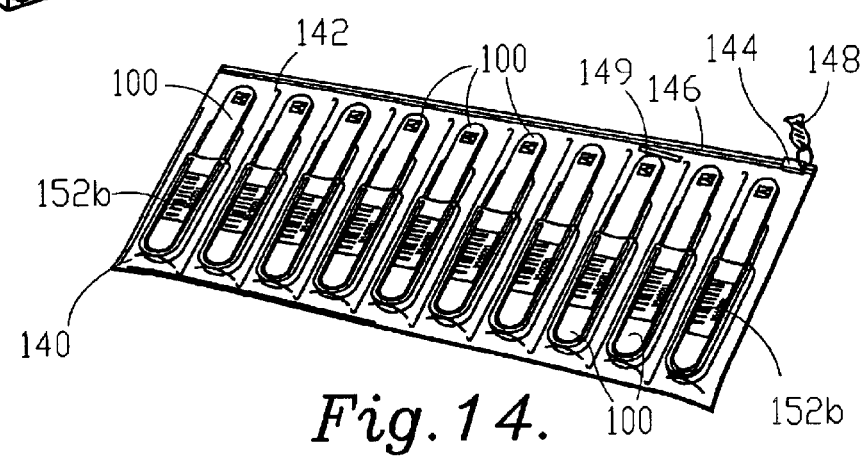
FIG. 14 is a front perspective view of an alternative embodiment of a storage system for a plurality of DNA collection devices having a bar code identifier available for scanning.

Referring now to FIGS. 13, 14 and 15, the apparatus and method of storing the DNA sample to allow correlation of the DNA sample with various evidentiary reports will be described. First referring to FIG. 15, a DNA collection device 100 is shown being inserted into a box 150 for storage. As is shown in FIG. 15, DNA collection device 100 has a bar code 152b attached to cover 104 of collection device 100. Bar code 152b corresponds to bar code 152a which is attached to storage box 150. It will be appreciated that bar code 152b, while being placed on cover 104 in FIG. 15, could as well be placed on collector 102. Also, it should be appreciated that the bar codes can be placed on the collection devices and/or the storage box at the time of manufacture or as the devices or boxes are used by the individual collecting a sample as is described hereinafter. The utility and relationship of the use and placement of bar codes 152a, 152b will now be described.

In the collection of evidence, and in particular, DNA evidence from individuals and from crime scenes, it is critical that the officers in charge of the crime scene or the subject from whom the DNA sample is being taken precisely identify the location from which the DNA sample is being taken, or the subject from whom the sample is being taken and identify the important related facts and reports related to the collection of the DNA sample. For example, if a DNA sample is being collected from a surface in a crime scene, the investigator will wish to document the exact location of the DNA sample within the crime scene and will wish to correlate the report which describes where the DNA was located with the actual DNA sample itself. In addition, the investigator will wish to correlate photographs which may have been taken of the crime scene and of the location at which one particular DNA sample was acquired. It will be appreciated that in any crime scene, it is possible that a number of different DNA samples may be taken and that those samples may produce DNA which identifies several different but unknown individuals. Therefore, it is necessary that the investigator be able to precisely document the location of each DNA sample and to correlate the actual DNA sample that was taken with the investigative materials and descriptive data acquired by the investigator. The present invention allows such a correlation between an actual DNA sample and investigative materials and evidentiary reports to be correlated as well as to provide a precise storage mechanism for retaining the various DNA samples that were collected at a crime scene over a long period of time. The present invention also permits the identification of specific DNA samples without disturbing the sample itself and without the need to break any seals that have been applied to evidentiary containers.

Specifically, in the collection of DNA from a subject or from a crime scene, it will be necessary for the investigator to act, generally, in the following manner. The investigator will identify the location in a crime scene from which a DNA sample is to be acquired. The investigator will then remove a DNA collection device 100 from its sealed package, remove cover 104 from collector 102 and will rub absorbent 110 on the area from which the DNA sample is to be acquired or on the individual from which the sample is to be taken. The investigator will then replace cover 104 and remove one of several bar code labels from a sample identification sheet (FIG. 16) that is associated with the particular DNA collection device 100 and on which investigation notes and/or sample identifying information or suspect information has been recorded. In FIG. 15, the bar code identified as bar code 152b would be obtained from the information sheet of Fig. 16 by removal of bar code 160 identified with the legend "place on DNA collector" on the information sheet of FIG. 16 and bar code 160 would be placed on collector 100 of Fig. 15 where it is shown as bar code 152b. Again, it will be appreciated that bar code 160 of information sheet of FIG. 16 could be positioned on collector 102 in FIG. 12. To identify box 150 of FIG. 15, the investigator would remove either one of extra bar codes 168 from the information sheet of FIG. 16, or if box 150 was to be used to ship the specimen to a laboratory for testing, the investigator could remove bar code label 166 of the information sheet of FIG. 16 which is identified as "place on specimen return envelop," and thereby, correlate box 150 now bearing bar code 166 of the information sheet of FIG. 16 which has been placed onto the position indicated by bar code 152a of FIG. 15. It will, of course, be appreciated by those skilled in the art that all the bar codes attached to the information sheet of FIG. 16 bear the same bar code number so that, as the bar codes are removed from the information sheet of FIG. 16 and placed on various storage containers or investigator reports or photographs or the DNA collection device 100 itself, all of the elements related to the DNA sample become associated or correlated together by the securing of the several identical bar code labels to each storage box or shipping container or investigative report or investigative photograph which is related to the DNA sample which was collected on DNA collection device 100.

In the situation in which a number of DNA specimens are collected from a particular crime scene, it may be desirable to retain all of the DNA collection devices 100 together so that all the DNA specimens associated with a particular crime scene location are retained together in a single storage location. Such a storage option can be obtained through the use of storage containers shown in FIGS. 13 and 14. First referring to FIG. 13, a storage case 130 is provided having multiple storage drawers 132 therein. Each storage drawer 132 is capable of receiving a bar code 134 which can be placed on the front of the drawer 132 for reading with a bar code scanner. Within each drawer 132 can be placed a DNA collection device 100 after a sample has been collected thereon. If the chain of evidence must be maintained for the DNA sample, the particular drawer 132 containing the sample can be secured with a band or sealing device 136 which passes through case 130 and through drawer 132 to prevent drawer 132 from being opened without breaking of seal 136. In this manner, if it is desired to identify a particular DNA collection device 100 which has been placed into one of drawers 132, the bar codes 134 may be read on each of drawers 132 to identify the particular drawer bearing the DNA collection device 100 which is actually sought. This can be accomplished without the need to break any of the seals 136 which are in place to assure the chain of custody requirements in criminal matters.

As an alternative storage method for retaining a smaller number of samples or samples which are all related to a single location, the storage device of FIG. 14 may be used which also allows for maintaining of the chain of custody for each of the DNA samples, but which also allows for the removal of any one particular DNA sample. The storage container 140 of FIG. 14 is provided with multiple individual pockets 142 which are sized to accept one DNA collection device 100. After insertion of the DNA collection devices within container 140, the entire container may be sealed by moving closure device 144 to a position at which it seals closure zipper 146 thereby closing container 140. If the chain of custody is to be maintained once closure device 144 has sealed container 140, a seal 148 may be attached to closure device 144 to prevent reopening of container 140 unless seal 148 is broken. When it is desired to identify one of the particular DNA collection devices 100 which is contained within container 140, bar codes 152b of each of DNA collection devices 100 may be read with a bar code scanner, and the particular DNA collection device 100 that is sought may be located. If it is desired to remove that single particular DNA collection device 100 from container 140, it is possible to do so without disturbing seal 148. In the manner which has been typically used with evidence bags when a sample or a portion of the evidence is to be removed by a particular investigator, a slit 149 may be made in container 140, and the particular DNA collection device 100 which is desired to be tested may be removed from container 140 and slit 149 sealed with tape bearing the investigator's name and date of removal of a sample to verify the date on which and by whom the sample is removed thereby maintaining the chain of custody.

In the manner that has been described, it will, therefore, be appreciated that by use of the present invention, DNA samples may be collected and those DNA samples may be correlated with various investigative reports and subject identification material and/or photographs which have been obtained of a subject or of a crime scene, and the DNA samples can be stored and the chain of evidence maintained and association with the descriptive materials written up by an investigator can be maintained during the course of investigation and trials related to the evidence collected.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

Having now described the features, discoveries and principles of the invention, the manner in which the inventive oral fluid collection device is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. An apparatus for the collection of a DNA sample comprising:
   a handle,
   an absorbent attached to said handle said absorbent having a first side and a second side,
   a carrier for receiving said handle and holding said handle therein,
   a cover to protect said absorbent, said cover having a vent therein, and
   a resilient member on said carrier, said resilient member extending adjacent to said absorbent second side to support said absorbent during DNA collection.

2. The apparatus as claimed in claim 1 wherein said carder further comprises a securing member to retain said handle within said carrier.

3. The apparatus as claimed in claim 1 wherein said handle is retained within said carrier by frictional fit of said handle within said carrier.

4. The apparatus as claimed in claim 1 wherein said handle further comprises a first handle portion and a second handle portion for capture of said absorbent therebetween.

5. An apparatus for the collection of a DNA sample comprising:
   a handle, said handle comprising a first handle portion and a second handle portion,
   an absorbent captured between said handle portions, said absorbent having a first side and a second side,
   a carrier for receiving said handle and holding said handle therein, and a support on said carrier, said support reinforcing said absorbent for DNA collection on said absorbent.

6. The apparatus as claimed in claim 5 further comprising a cover to protect said absorbent.

7. The apparatus as claimed in claim 6 further comprising a vent.

8. The apparatus as claimed in claim 5 wherein said carrier further comprises a securing member to retain said handle within said carrier.

9. The apparatus as claimed in claim 8 wherein said handle is retained within said carrier by frictional fit.

10. A method of collecting of a DNA sample from the oral cavity of a subject comprising:

providing an absorbent having a first side and a second side, attaching said absorbent to a holder, mounting, removably, said absorbent holder containing said absorbent in a carrier, said carrier supporting said absorbent second side, inserting said supported absorbent into the buccal cavity of the subject, rubbing said absorbent first side against the cheek of the subject, and allowing cheek epithelial cells to collect on said absorbent.

11. The method as claimed in claim 10 further comprising the step of placing a cover over said absorbent.

* * * * *